(12) United States Patent
Chmielewski

(10) Patent No.: US 9,533,975 B2
(45) Date of Patent: Jan. 3, 2017

(54) DUAL-ACTION, UNNATURAL PROLINE-RICH PEPTIDES AS ANTIBIOTIC AGENTS AND METHODS THEREOF

(71) Applicant: Purdue Research Foundation, West Lafayette, IN (US)

(72) Inventor: Jean Anne Chmielewski, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 14/702,530

(22) Filed: May 1, 2015

(65) Prior Publication Data

US 2015/0314009 A1 Nov. 5, 2015

Related U.S. Application Data

(60) Provisional application No. 61/987,140, filed on May 1, 2014.

(51) Int. Cl.

| | |
|---|---|
| *C07K 7/06* | (2006.01) |
| *C07D 405/14* | (2006.01) |
| *A61K 47/48* | (2006.01) |
| *A61K 31/7036* | (2006.01) |
| *A61K 49/00* | (2006.01) |
| *C07K 5/083* | (2006.01) |
| *A61K 38/00* | (2006.01) |

(52) U.S. Cl.
CPC ......... *C07D 405/14* (2013.01); *A61K 31/7036* (2013.01); *A61K 47/48238* (2013.01); *A61K 49/0056* (2013.01); *C07K 5/0806* (2013.01); *A61K 38/00* (2013.01)

(58) Field of Classification Search
CPC ........................................................ C07K 7/06
USPC ........................................ 530/328, 329, 330
See application file for complete search history.

(56) References Cited

PUBLICATIONS

Fillon, Y., et al., Cell Penetrating Agents Based on a Polyproline Helix Scaffold. J. Am. Chem. Soc. 2005, 127, 11798-11803.
Daniels, D., et al., Intrinsically Cell-Permeable Miniature Proteins Based on a Minimal Cationic PPII Motif. J. Am. Chem. Soc. 2007, 129, 14578-14579.
Fernandex-Carneado, J., et al., Potential Peptide Carriers: Amphipathic Proline-Rich Peptides Derived from the N-Terminal Domain of g-Zein. Angew. Chem. Int. Ed. 2004, 43, 1811-1814.
Potocky, T., et al., HeLa Cell Entry by Guanidinium-Rich b-Peptides: Importance of Specific Cation-Cell Surface Interactions. ChemBioChem 2007, 8, 917-926.
Li, L., et al., Cationic amphiphilic polyproline helix P11LRR targets intracellular mitochondria. Journal of Controlled Release 142 (2010) 259-266.
Madani, F., et al., Mechanisms of Cellular Uptake of Cell-Penetrating Peptides. Journal of Biophysics. 2011, Article ID 414729.
Duchardt, F., et al., A Comprehensive Model for the Cellular Uptake of Cationic Cell-penetrating Peptides. Traffic 2007; 8: 848-866.
Geisler, I., et al., Probing length effects and mechanism of cell penetrating agents mounted on a polyproline helix scaffold. Bioorganic & Medicinal Chemistry Letters 17 (2007) 2765-2768.
Geisler, I., et al., Dimeric Cationic Amphiphilic Polyproline Helices for Mitochondrial Targeting. Pharm Res (2011) 28:2797-2807.
Ranjan, A., et al., Efficacy of Amphiphilic Core-Shell Nanostructures Encapsulating Gentamicin in an In Vitro *Salmonella* and *Listeria* Intracellular Infection Model. Antimicrobial Agents and Chemotherapy, Aug. 2010, p. 3524-3526.
Pereira, M. et al., Maximizing the Therapeutic Window of an Antimicrobial Drug by Imparting Mitochondrial Sequestration in Human Cells. J. Am. Chem. Soc. 2011, 133, 3260-3263.
Imbuluzqueta, E., et al., Novel bioactive hydrophobic gentamicin carriers for the treatment of intracellular bacterial infections. Acta Biomaterialia 7 (2011) 1599-1608.
Horton, K., et al., Mitochondria-Penetrating Peptides. Chemistry & Biology 15, 375-382, (2008).
Shai, Y., Mode of Action of Membrane Active Antimicrobial Peptides. Biopolymers (Peptide Science), vol. 66,236-248 (2002).
Brogden, K., Antimicrobial Peptides: Pore Formers or Metabolic Inhibitors in Bacteria? Nature Reviews | Microbiology, vol. 3 | Mar. 2005 | 238-250.
Zasloff, M., Antimicrobial peptides of multicellular organisms. Nature |vol 415 | 2002,389-395.
Wang, G., et al., APD2: the updated antimicrobial peptide database and its application in peptide design. Nucleic Acids Research, 2009, vol. 37, Database issue D933-D937.
Chongsiriwatana, N., et al., Peptoids that mimic the structure, function, and mechanism of helical antimicrobial peptides. PNAS, 2008, vol. 105, No. 8, 2794-2799.
Hansen, A., et al., Intracellular Toxicity of Proline-Rich Antimicrobial Peptides Shuttled into Mammalian Cells by the Cell-Penetrating Peptide Penetratin. Antimicrobial Agents and Chemotherapy, 2012, vol. 56, p. 5194-5201.
Kuriakose, J., et al., Targeting Intracellular Pathogenic Bacteria with Unnatural Proline-Rich Peptides: Coupling Antibacterial Activity with Macrophage Penetration. Angew. Chem. Int. Ed. 2013, 52, 9664-9667.
Seleem, M., et al., TargetingBrucellamelitensiswith polymeric nanoparticles containing streptomycinand doxycycline. FEMS Microbiol Lett 294 (2009) 24-31.
Corrigan, R., et al., An improved tetracycline-inducible expression vector for *Staphylococcus aureus*. Plasmid 61 (2009) 126-129.
Boman, H., et al., Mechanisms of Action on *Escherichia coli* of Cecropin P1 and PR-39, Two Antibacterial Peptides from Pig Intestine. INFECrION and Immunity, 1993, vol. 61(7), p. 2978-2984.
Hsu, C., et al., Structural and DNA-binding studies on the bovine antimicrobial peptide, indolicidin: evidence for multiple conformations involved in binding to membranes and DNA. Nucleic Acids Research, 2005, vol. 33, No. 13, 4053-4064.

(Continued)

*Primary Examiner* — David Lukton
(74) *Attorney, Agent, or Firm* — Faegre Baker Daniels LLP

(57) ABSTRACT

The present invention cationic amphiphilic polyproline helices (CAPHs) compounds having increased hydrophobicity and cellular internalization as antimicrobial agents. Antimicrobial compositions and methods of using the same are also provided.

18 Claims, 1 Drawing Sheet

(56) References Cited

PUBLICATIONS

Kitagawa, M., et al., Complete set of ORF clones of *Escherichia coli* ASKA library (A Complete Set of *E. coli* K-12 ORF Archive): Unique Resources for Biological Research. DNA Research 12, 291-299 (2005).

Pathania, R., et al., Chemical genomics in *Escherichia coli* identifies an inhibitor of bacterial lipoprotein targeting. Nature Chemical Biology, vol. 5 No. 11, 2009, 849-856, (2009).

Scocchi, M., et al., The Proline-rich Antibacterial Peptide Bac7 Binds to and Inhibits in vitro the Molecular Chaperone DnaK. Int J Pept Res Ther (2009) 15:147-155.

Nair, D., et al., Whole-Genome Sequencing of *Staphylococcus aureus* Strain RN4220, a Key Laboratory Strain Used in Virulence Research, Identifies Mutations That Affect Not Only Virulence Factors but Also the Fitness of the Strain. Journal of Bacteriology, May 2011, p. 2332-2335.

Wender, P., et al., The design, synthesis, and evaluation of molecules that enable or enhance cellular uptake: Peptoid molecular transporters. PNAS, 2000, vol. 97, No. 24, 13003-13008.

Futaki, S., et al., Membrane-permeable arginine-rich peptides and the translocation mechanisms. Advanced Drug Delivery Reviews 57 (2005) 547-558.

Vives, E., Present and future of cell-penetrating peptide mediated delivery systems: "Is the Trojan horse too wild to go only to Troy?" Journal of Controlled Release 109 (2005) 77-85.

Lewin, M., et al., Tat peptide-derivatized magnetic nanoparticles allow in vivo tracking and recovery of progenitor cells. Nature Biotechnology, 2000, vol. 18, 410-414.

Wadia, J., et al., Transmembrane delivery of protein and peptide drugs by TAT-mediated transduction in the treatment of cancer. Advanced Drug Delivery Reviews 57 (2005) 579-596.

Chung, H., et al., Dendritic Oligoguanidines as Intracellular Translocators. Biopolymers (Peptide Science), vol. 76, 83-96 (2004).

Degols, G., et al., Oligonucleotide-Poly(L-lysine)-Heparin Complexes: Potent Sequence-Specific Inhibitors of HIV-1 Infection. Bioconjugate Chem. 1994, 5, 8-13.

Kalafut, D., et al., Mitochondrial targeting of a cationic amphiphilic polyproline helix. Bioorganic & Medicinal Chemistry Letters 22 (2012) 561-563.

Kumarasamy, K., et al., Emergence of a new antibiotic resistance mechanism in India, Pakistan, and the UK: a molecular, biological, and epidemiological study. Lancet Infect Dis 2010;10: 597-602.

Briones, E., et al., Delivery systems to increase the selectivity of antibiotics in phagocytic cells. Journal of Controlled Release 125 (2008) 210-227.

Ragin, A., et al., Cellular Import Mediated by Nuclear Localization Signal Peptide Sequences. Chemistry & Biology, vol. 8, 943-948 (2002).

Ragin, A., et al., Probing essential residues for cellular uptake with a cationic nuclear localization signal sequence. J. Peptide Res., 2004, 63, 155-160.

Li, X., et al., Multicopy Suppressors for Novel Antibacterial Compounds Reveal Targets and Drug Efflux Susceptibility. Chemistry & Biology, vol. 11, 1423-1430 (2004).

Mitchell, D., et al., Polyarginine enters cells more efficient than other polycationic homopolymers. J. Peptide Res., 2000, 56, 318-325.

Rothbard, J., et al., Conjugation of arginine oligomers to cyclosporin A facilitates topical delivery and inhibition of inflammation. Nature Medicine • vol. 6 • No. 11 • 2000, 1253-1257.

Futaki, S., et al., Arginine-rich Peptides. The Journal of Biological Chemistry, vol. 276, No. 8, Issue of 2001, pp. 5836-5840.

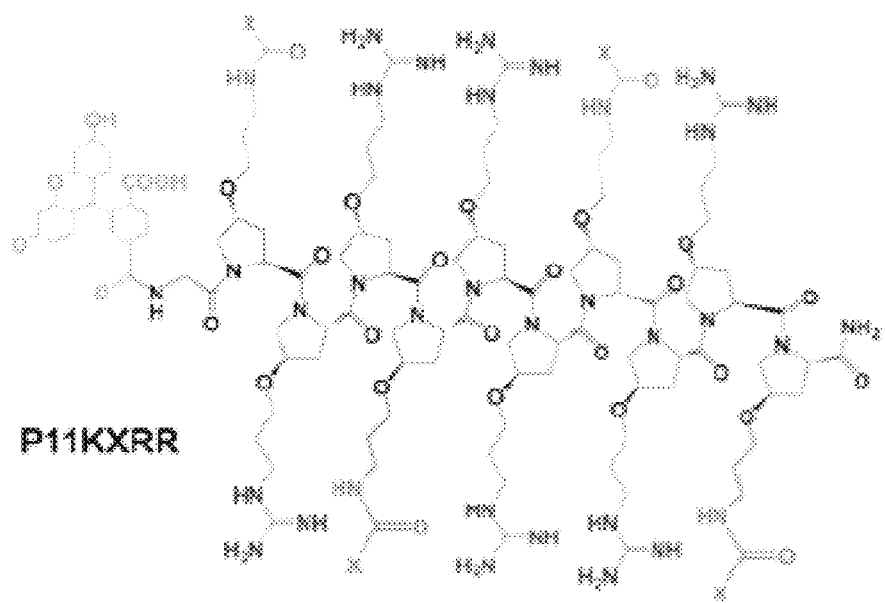

DUAL-ACTION, UNNATURAL PROLINE-RICH PEPTIDES AS ANTIBIOTIC AGENTS AND METHODS THEREOF

CROSS-REFERENCE TO RELATED APPLICATIONS

This application claims the benefit of priority under 35 U.S.C. 119(e) of U.S. Provisional Application Ser. No. 61/987,140, filed on May 1, 2014, the content of which relied upon and incorporated herein by reference in its entirety.

GOVERNMENT RIGHTS

This invention was made with government support under CHE1012316 awarded by the National Science Foundation. The government has certain rights in the invention.

BACKGROUND OF THE INVENTION

The present invention relates generally to antimicrobial agents, and particularly to cationic amphiphilic polyproline helices as antimicrobial agents.

The emergence of drug resistant bacteria is a growing challenge to anti-infective therapy. Pathogens such as methicillin- and vancomycin-resistant *Staphylococcus aureus* (MRSA and VRSA), and resistant *Pseudomonas aeruginosa* and *Acinetobacter baumanni* have undermined most, and sometimes all, clinically usable antibacterial drugs. As new bacterial strains continue to evolve, the concomitant discovery of novel antibacterial agents has drastically lagged behind. Furthermore pathogens such as *Bacillus anthracis* and *Brucella*, classified as bioterrorism agents, pose an ongoing threat to security. The generation of new antibacterial agents with novel mechanisms of action, therefore, is of high importance.

Another challenge in the development of effective antibacterial agents arises from bacterial pathogens that have evolved to inhabit mammalian cells, such as phagocytic macrophages. Within these intracellular safe havens the bacteria reproduce and form a repository, causing recurrent infections. Such intracellular pathogenic bacteria include *Mycobacterium tuberculosis, Salmonella, Listeria, Legionella* and *Brucella*. When localized within mammalian cells, bacteria are able to evade the host immune response as well as a number of antibiotic drugs. A significant subset of antibiotics, such as p-lactams and aminoglycosides, are unable to achieve therapeutic concentrations within the host cell due to poor cell permeability and/or efflux transporters. These difficulties have spurred efforts to target intracellular pathogens using delivery vehicles such as liposomes and nanoparticles containing antibiotics.

Antimicrobial peptides (AMPs) are evolutionarily conserved molecules produced widely by plants and animals to defend against microbes. The majority of AMPs exert their antibiotic effect by targeting the microbial cell membrane resulting in cell lysis. This mechanism of action is a major drawback for clinical use of AMPs due to host cell toxicity. However, a small class of non-membrane lytic AMPs have been identified that have a high proline content and an overall cationic charge due to high levels of arginine, such as bactenectin, PR-39, apidaecin, pyrrhocoricin and drosocin. These proline-rich AMPs (P-AMPs) predominantly target Gram negative bacteria, while having minimal effect on Gram positive strains. In some cases the intracellular targets of P-AMPs have been identified such as the heat shock protein DnaK. While P-AMPs are less toxic than membrane-lytic AMPs, as seen in their lack of hemolytic activity and safety in animal models, the majority do not enter mammalian cells, with a few exceptions.

The plasma membrane of cells presents a formidable barrier to the passage of a number of therapeutic agents and probes. The passive uptake of genes, polypeptides and particles into cells is prohibitive due to size constraints, although smaller oligonucleotides and peptides are also too hydrophilic to adequately cross the hydrophobic bilayer. (Dokka, S. et al. (2000) Advanced Drug Delivery Reviews 44, 35-49; Juliano, R. (2007) Biochemical Society Transactions 35, 41-3.) The cell impermeable nature of these biopolymers and nanostructures serves to underscore the need to develop efficient strategies for their cellular uptake. A key feature to novel approaches is an understanding of the mechanism of cell penetration, so that better agents may be designed.

A number of different approaches have been taken to accomplish the delivery of therapeutic agents into cells. One recent approach has been the use of cell penetrating peptides (CPPs) that are rich in basic amino acids. (Fischer, R. et al. (2005) Chem. BioChem. 6, 2126-42; Futaki, S. (2005) Advanced Drug Delivery Reviews 57, 547-58; Vives, E. (2005) Journal of Controlled Release 109, 77-85.) CPPs have many advantageous features: generally low toxicity, high efficiency toward a variety of different cell lines, as well as the delivery of diverse cargo to intracellular targets reaching from proteins and oligonucleotides to magnetic nanoparticles. Two of the most well studied CPPs, derived from transcription factors, include the cationic domain of HIV-Tat (Tatp, GRKKRRQRRR)35 and the penetratin peptide from the Antennapedia homodomain. (Derossi, D. et al. (1994) Journal of Biological Chemistry 269, 10444-50; Derossi, D. et al. (1996) The Journal of Biological Chemistry 271, 18188-93; Prochiantz, A. (1996) Current Opinion in Neurobiology 6, 629-34.) Other short peptides used for membrane translocation include: cationic nuclear localization signal sequences, polylysine or polyarginine peptides, short peptides of alternating Arg and hydrophobic residues, peptides derived from the y-zein protein and other proline-rich sequences, and cationic moieties linked to scaffolds, such as peptoids, β-amino acid peptides, oligocarbamates, loligomers, dendrimers and biphenyls.

As can be seen, there is a need for effective antimicrobial agents, particularly those that can enter mammalian cells. While natural and synthetic peptides show promise as antimicrobial agents, it would desirable to have a peptide based antimicrobial agent that can enter mammalian cells by a number of different mechanisms, is toxic to microbes while sparing the host mammalian cell.

SUMMARY OF THE INVENTION

In one aspect of the present there is provided a compound having the structure:

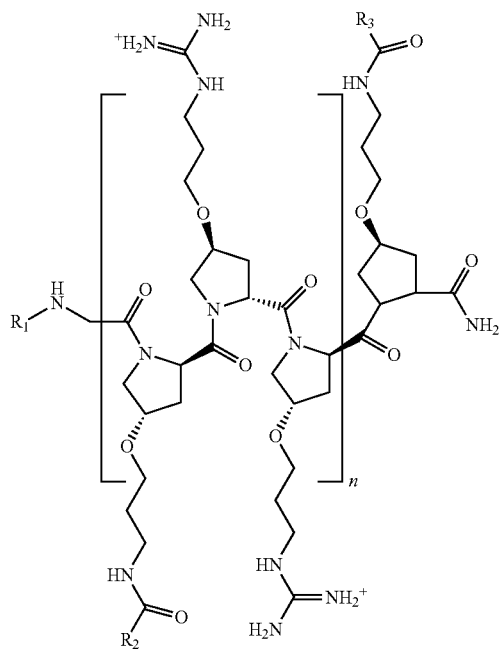

wherein $R_1$ is an alkyl substituent, the alkyl substituent being straight, branched or cyclic, an aryl substituent, a dye, a fluorophore, a conjugating agent or an antimicrobial agent; $R_2$ and $R_3$ are each independently, a hydrophobic alkyl or aryl moiety and n is from about 3 to about 10.

In another aspect of the present invention there is provided a compound having the structure:

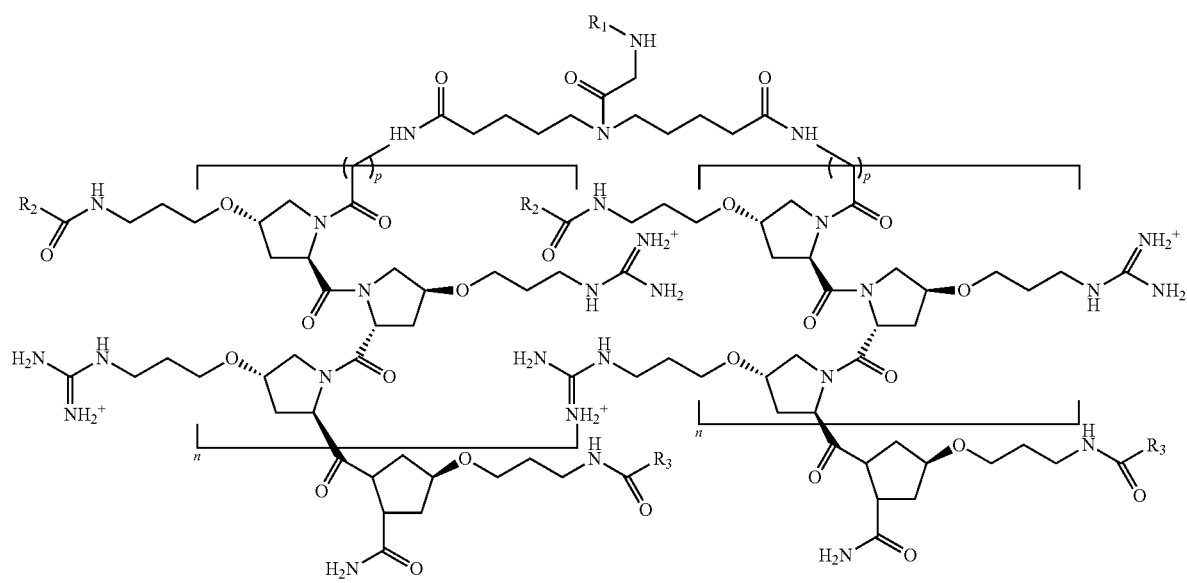

wherein $R_1$ is an alkyl substituent, the alkyl substituent being straight, branched or cyclic, an aryl substituent, a dye, a fluorophore, a conjugating agent or an antimicrobial agent; $R_2$ and $R_3$ are each independently, a hydrophobic alkyl or aryl moiety; n is from about 3 to about 10 and p is from about 1 to about 5.

In another aspect of the present invention there are provided antimicrobial compositions comprising the compounds of the present invention. It has been found that the compounds of the present invention are effective antimicrobial agents, particularly against intracellular microbes, while not harming the host cell.

These and other features, aspects and advantages of the present invention will become better understood with reference to the following drawings, description and claims.

BRIEF DESCRIPTION OF THE DRAWINGS

FIG. 1 is a schematic showing examples of compound (I) of the present invention.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention provides cationic amphiphilic polyproline helices (CAPHs) that act both as cell penetrating agents and as antimicrobial agents. These properties allow the CAPHs of the present invention to penetrate a host cell, destroy the microbe invading the host cell with minimal cytotoxicity to the host cell. It is contemplated that the host cell may be mammalian or animal cell, including, but not limited to, human, dog, cat, horse and bird. It will be appreciated that the CAPH compounds of the present invention may be used in both human and veterinary applications.

While CAPHs are known in the prior art, the CAPHs of the present invention have been modified to allow for increased hydrophobicity of the CAPHs. While not wishing to be bound by theory, increased hydrophobicity may increase cellular uptake. Manipulation of the hydrophobicity may also effect the method of cellular uptake and therefore, cellular localization. Previously, the proline moieties of the CAPHs were modified using an ether linkage (Scheme 1). In the present invention, an amide linkage may be used instead of the ether linkage, allowing for a wide diversity of hydrophobic substituents to be added to the CAPHs of the present invention.

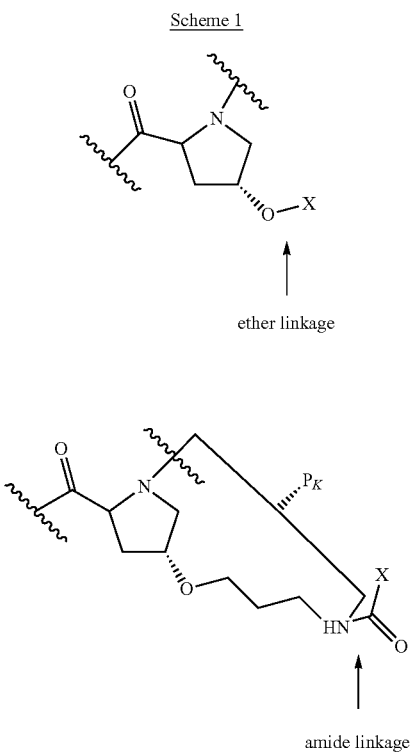

Scheme 1 ether linkage amide linkage

In one embodiment of the present invention there is provided compound (I) having the structure:

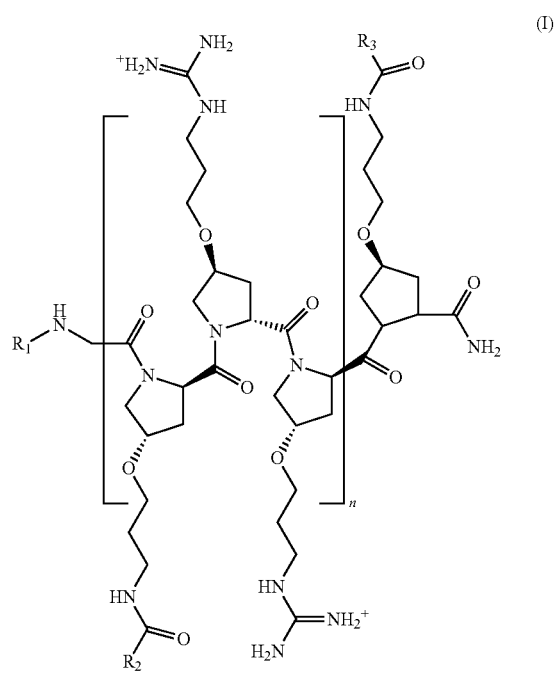

wherein $R_1$ may be an alkyl substituent, the alkyl substituent being straight, branched or cyclic, an aryl substituent, a dye, a fluorophore, a conjugating agent or an antimicrobial agent;

$R_2$ and $R_3$ may each independently be, a hydrophobic alkyl or aryl moiety and n may be from about 3 to about 10.

In one embodiment of the present invention n may be from about 3 to about 10 repeats. Preferably, n may be from about 3 to about 5 repeats. By increasing number of repeats (n) corresponding to the length of the CAPH, additional cationic and hydrophobic groups may be introduced into the helix. An increase of just one repeat from n=3 to n=4 may increase cellular permeation as well as effect the internalization mechanism and subcellular localization of the CAPH of the present invention. CAPHs may be internalized in a number of different ways including, but not limited to endocytosis and direct transport. When internalized of the CAPH of the present invention by endocytosis may result in endosomal entrapment of the CAPH. Direct transport, however, may allow for the CAPH to be localized in a specific, desired subcellular localization. While not wishing to be bound by theory, it has been found that increasing number of repeats or length of the CAPH allows for internalization by direct transport at lower concentrations of the CAPH.

The CAPH compounds of the present invention may comprise other molecules that may allow for the monitoring of subcellular localization, may help direct subcellular localization and/or may allow for direct binding to a moiety within the host cell. In one embodiment of the present invention, $R_1$ may be an alkyl or aryl moiety, preferable one that increases the cationic or hydrophobic propertied of the compound of the present invention. Alternatively, $R_1$ may be a fluorophore or fluorescent molecule that allows for the tracking of the subcellular location of the compound. A non-limiting example may be fluorescein. Likewise, $R_1$ may be any molecule that allows for tracking and detection of the molecule in the host cell. It will be appreciated that there are many compounds that may be used including dye molecules and those containing radioactive markers.

Alternative, $R_1$ may be compounds that direct subcellular localization by binding covalently or non-covalently to proteins, membranes or other subcellular organelles or moieties. Conjugating agents may be crosslinking agents, a plethora of which is known in the art. They may also be binding agents, such as but not limited to biotin. In a preferred embodiment $R_1$ may be intracellular directing groups such as, but not limited to actin binding sequence and endoplasmic reticulum binding sequence. By way of non-limiting example, when *Listeria* invades a host cell, it is usually located in the macrophages where more antimicrobial agents cannot act upon it. $R_1$ may be an actin binding sequence, allowing for the subcellular localization of the CAPH of the present invention in the macrophages and allowing it to destroy *Listeria*.

In a further embodiment of the present invention, $R_1$ may be a second antimicrobial agent, thereby increasing the potency of the CAPH compounds of the present invention. Antimicrobial agents are well known in the art and the skilled artisan may link these antimicrobial agents to the compounds of the present invention using methods known in the art without undue experimentation. Presented as a non-limiting example, compound (II) illustrated kanamycin bound to a CAPH through a disulfide tether.

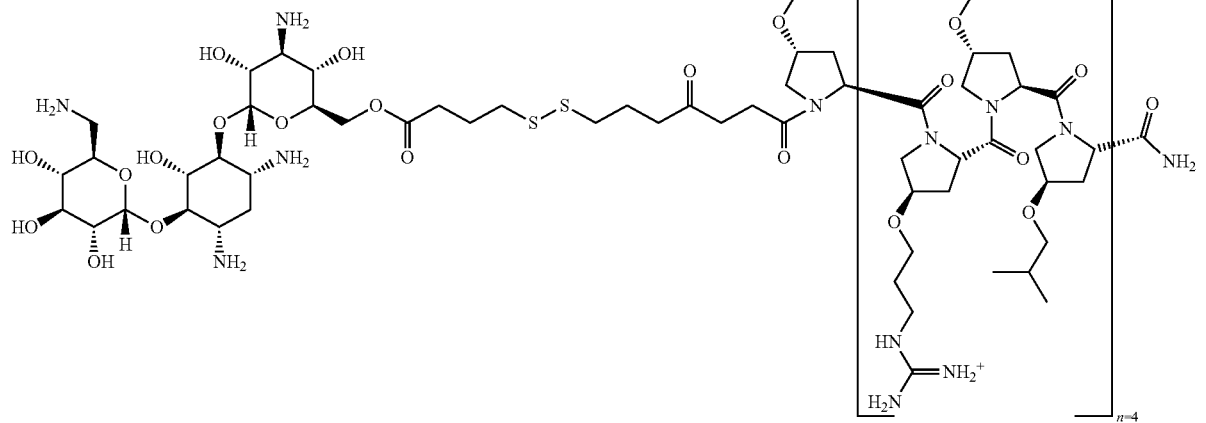

(II)

In another embodiment of the present invention, $R_2$ and $R_3$ may be, each independent of the other, alkyl or aryl substituents. These alkyl or aryl substituents may increase the hydrophobicity of the CAPH compounds of the present invention. In one embodiment, $R_2$ and $R_3$ may each independently be an alkyl substituent wherein the alkyl substituent may be straight chained, branched or cyclic. The alkyl substituent may further comprise heteroatoms or, in the case of cyclic alkyl substituents, may also further comprise fused ring structures. The alkyl substituents of the present invention may comprise from about 1 carbon to about 20 carbons, from about 2 carbons to about 15 carbons or from about 5 carbons to about 10 carbons. Non-limiting examples of alkyl substituents may be n-heptyl, n-pentyl, iso-pentyl, iso-heptyl, cyclohexyl or cyclooxyl. It will be appreciated that these examples are given by way of illustration and not meant to be limiting.

In an alternate embodiment, $R_2$ and $R_3$ may be aryl substituents. Aryl substituents may be from about 5 carbons to about 8 carbons. The aryl substituents of the present invention may be heterocyclic and/or they may comprise substituents on the aryl ring. Substituents on the ring may be, but not limited to, alkyls (both straight chained and branched), alkoxy, hydroxyl, nitro, nitrile and other substituents known in the art. In one embodiment, the substituents may be electron donating or electron withdrawing. Non-limiting example of aryl substituents may be phenyl, methoxyphenyl or nitrophenyl.

The present invention further provides dimeric structures of the compounds of the present invention comprising two molecules of compound (1) and wherein $R_1$ is a linker.

The present invention also provides a dimeric CAPH having the structure of compound (III):

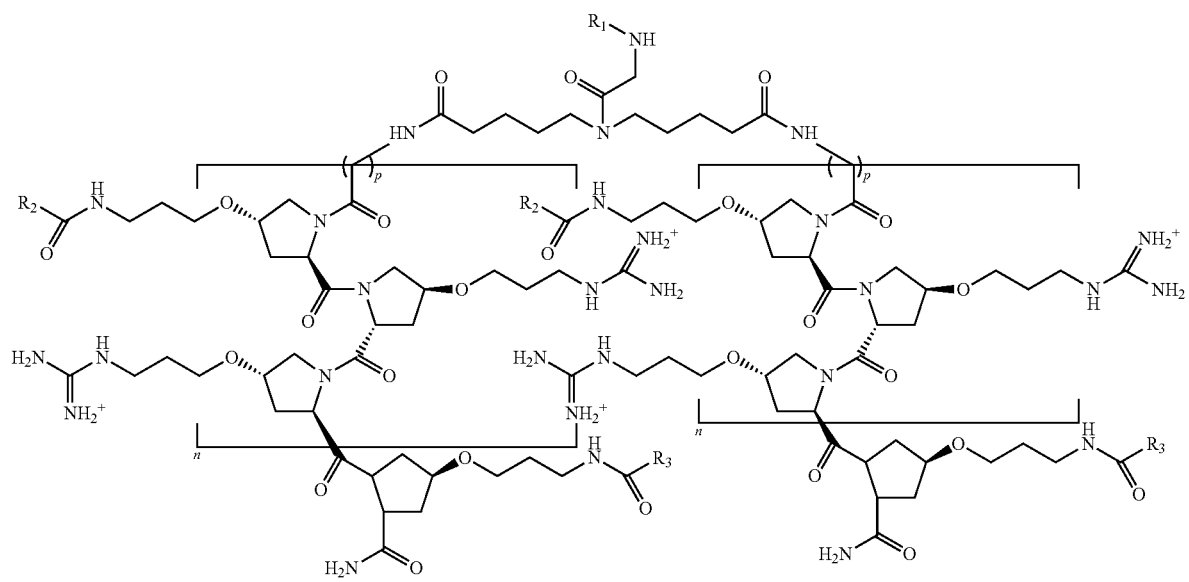

wherein $R_1$ is an alkyl substituent, the alkyl substituent being straight, branched or cyclic, an aryl substituent, a dye, a fluorophore, a conjugating agent or an antimicrobial agent; $R_2$ and $R_3$ are each independently, a hydrophobic alkyl or aryl moiety; n is from about 3 to about 10 and p is from about 1 to about 5. $R_1$, $R_2$, $R_3$ and n are defined as for compound (I). In one embodiment, p may be from about 1 to about 5 or from about 1 to about 3. The length of the linker may not be critical for cellular internalization of compound (III). It will be appreciated that by linking together two molecules of compound (I), the overall hydrophobicity of the compound (III) is increased and may result in more effective subcellular localization over the monomeric form, compound (I).

In another embodiment of the present invention there are provided antimicrobial compositions comprising compound (I), compound (III) or both. The antimicrobial compositions of the present invention may further comprise other antimicrobial agents, a carrier or buffer or any other compound commonly used in antimicrobial compositions. The antimicrobial compositions may be a solution, a suspension or a solid.

The present invention also provides methods for treating a host cell having a microbial infection comprising the steps of administering compound (I), compound (II) or a mixture of both to the host cell having the microbial infection. It will be appreciated that there may be a mixture, for example but not limited to, of different compound (I) having different substituents. It will also be appreciated from the foregoing discussion that $R_1$ may be chosen according to the microbial infection to be treated. Methods of the present invention further provide methods for treating a patient, either mammal or animal, having a microbial infection with the compounds of the present invention. The exact compound will depend on the microbial infection of the patient. The amount of compound to be administered will depend on the infection and the type and size of the patient. The amount to be administered may be determined by the skilled artisan without undue experimentation.

Examples

Modifications to CAPHs were investigated in an effort to enhance cell penetration, to probe subcellular localization, and to determine the role of the hydrophobic group on the mechanism of cell entry. An alternative method was developed to incorporate the hydrophobic moiety into CAPHs to facilitate these studies. Previously an ether linkage had been used between the proline amino acid and the hydrophobic moieties (Scheme I). This was a successful approach for the development of CAPHs, but the ether-based approach limited the ability to prepare a diverse library of CAPHs quickly, as a new amino acid was needed for the synthesis of each peptide. To remedy this deficiency, and allow for the facile preparation of focused libraries of CAPHs, the use of an amide linkage between an amino-modified proline residue (PK) and the hydrophobic group was developed (Scheme I). In this way MTT protected PK residues were incorporated into a CAPH on resin, followed by on-resin deprotection of the MTT protecting group and acylation of the resulting amine with the desired carboxylic acid. Cleavage of the peptide from the resin provided a series of alkyl- and aromatic-modified CAPHs in parallel from the starting resin bound peptide (FIG. 1).

The series of alkyl-modified CAPHs were evaluated for cell uptake. The n-heptyl- and cyclohxylmodified CAPHs (FIG. 1; P11KC7RR and P11KC6CRR) were the most effective, displaying approximately a 10- and 5-fold increase in HeLa cell penetration, respectively, at 10 µM as compared to CAPHs previously reported in the literature. The subcellular localization of P11KC5RR and P11KC7RR was analyzed with HeLa cells at 5-15 µM. P11KC5RR was mainly localized to endosomes at 5-10 µM, but some mitochondrial localization was observed at 15 µM. P11 KC7RR, on the other hand localized to the mitochondria at all concentrations analyzed, with some nuclear localization detected at 10-15 µM.

A series of aryl-modified CAPHs with varying electron donating or withdrawing groups was also investigated (H, $NO_2$, $OCH_3$, FIG. 1) to probe the effect of the electronic character of the phenyl moiety. These CAPHs all displayed enhanced cellular penetration, with 3- to 6-fold increases in cellular uptake over known compounds at 10 µM. The CAPH containing the most electron-rich phenyl group appended to the PK residue, P11 KFOCH3RR, was the most effective. The subcellular localization in HeLa cells treated with 5-15 µM of the three CAPHs was also investigated. These CAPHs were localized to endosomes at all concentrations, with P11KFNO2RR displaying some nuclear localization at 15 µM. Overall, these data demonstrate that significant increases in cell penetration may be obtained through modifications to the hydrophobic moiety, using the newly developed synthetic strategy. Differences in subcellular localization were evident with the different types of hydrophobic groups, with alkyl chains favoring mitochondrial localization through direct transport, and the phenyl-modified CAPHs localizing to endosomes and the nucleus.

Antimicrobial peptides (AMPs) are a class of antibiotics that generally act by targeting microbial cell membranes resulting in cell lysis. This mechanism of action is also one of the major drawbacks associated with clinical use of AMPs due to host cell toxicity. However, a small class of non-membrane lytic AMPs have been identified. Unifying features of these non-membrane lytic AMPs are a high proline content and an overall cationic charge due to high levels of arginine. Proline-rich AMPs (P-AMPs) are less toxic than membrane-lytic AMPs, but most P-AMPs do not enter mammalian cells.

The interplay of structure and function for P-AMPs with idealized, de novo designed sequences has been investigated. P11LRR and P14LRR for antibacterial activity has been evaluated and a series of peptides starting with a sequence containing four copies of the PRP triad repeat found in natural P-AMPs, FI-PRP-4, and sequences with more cationic PRR-like triad (FI-PRR-4 and FI-PP$_R$P$_R$-4) has been designed in an effort to improve mammalian cell uptake. This latter sequence contains all proline-based residues, including the unnatural guanidinium-containing amino acid PR, but lacks the additional hydrophobic groups of P11 LRR and P14LRR. The CD spectrum of FI-PP$_R$P$_R$-4, P11 LRR and P14LRR each displayed a strong peak at 225 nm, characteristic of a PPII helix. FI-PRP-4 and FI-PRR-4, however, exhibited very weak maxima at 225 nm.

The antibacterial activity of the five peptides was explored with *E. coli* and *S. aureus*. Two of the most cationic peptides (P14LRR and FI-PRR-4) were the most active against both bacterial strains (Table 1). Electrostatic interactions between cationic AMPs and the negatively charged bacterial membrane are believed to be the first step in antibacterial action, thereby explaining the improved antibacterial activity when going from P11 LRR (+4 charge) to P14LRR (+8 charge). Interestingly, restricting FI-PRR-4 to a rigid PPII conformation had a detrimental effect on activity, as seen with FI-PPRPR-4. However, the addition of hydrophobic isobutyl groups to the proline backbone of (P14LRR) resulted in a dramatic improvement in activity against both bacteria (Table 1). Replacing the fluorescein moiety in P14LRR with an acetyl group led to no discernible change in activity.

TABLE 1

Antibacterial and hemolysis activity of designed P-AMPs

|  | E. coli MIC[a] [μM] | S. aureus MIC [μM] | Hemolysis [μM] |
|---|---|---|---|
| Fl-PRP-4 | >100 | >100 | >100 |
| Fl-PRR-4 | 40 | 20 | >100 |
| Fl-PP$_R$P$_R$-4 | 60 | >100 | >100 |
| P11LRR | 60 | 60 | >100 |
| P14LRR | 4 | 12 | >100 |
| Melittin | 4.6 | 2.1 | 5[b] |

[a]The minimum inhibitory concentration (MIC).
[b]Greater than 80% hemolysis was observed at this concentration.

Importantly, the designed P-AMPs caused only low levels of damage to human red blood cells (hRBCs) (<5%) after 1 h of incubation up to a concentration of 100 pM (Table 1), whereas melittin was highly hemolytic at 5 'LIM. This lack of observed hemolysis with the designed P-AMPs is a crucial feature for potential applications. P14LRR was therefore identified as the most potent, non-hemolytic antibacterial among the designed proline-rich peptides. P14LRR also has potent broad-spectrum antibacterial activity against methicillin-resistant *S. aureus* (MRSA) (8 pM), *B. anthracis* (8 pM) and the biofilm-forming clinical-isolates of *P. aeruginosa* and *S. aureus*. P14LRR was further shown to inhibit the growth of *Salmonella, Listeria* and *Brucella*, all classified as intracellular pathogens.

To rescue mammalian cells infected with intracellular bacteria, antimicrobial agents need to effectively penetrate within these host cells. The cell penetrating ability of all five peptides by flow cytometry with J774A.1 macrophage cells was evaluated. Macrophages are commonly invaded by intracellular bacteria and were thus selected for uptake studies. The three peptides (FI-PRR-4, FI-PPRPR-4, P14LRR) with the highest cationic charge (+8) showed significantly higher cellular fluorescence as compared to PII LRR (+6) and FI-PRP-4 (+4). The fluorescence associated with FI-PPRPR-4 uptake, however, was mostly due to cell surface binding. Among the most cationic peptides, there was approximately a four-fold increase in uptake in going from FI-PRR-4 to P14LRR. Thus among the designed P-AMPs, P14LRR was found to be most potently internalized within J774A.1 macrophage cells, without compromising the integrity of the cellular membranes. P14LRR was also found to satisfy two vital properties for application against intracellular bacteria: minimal toxicity towards J774A.1 macrophage cells and resistance to proteolytic degradation by trypsin.

With a knowledge of the separate cell penetrating and antibacterial activities of P14LRR, the ability of this P-AMP to clear intracellular bacterial pathogens, *Salmonella* and *Brucella*, within J774A.1 cells has been investigated using an in vitro bacterial protection assay. Intracellular *Salmonella* and *Brucella* were significantly reduced by 62% and 90% with the addition of P14LRR, respectively.

It should be understood, of course, that the foregoing relates to exemplary embodiments of the invention and that modifications may be made without departing from the spirit and scope of the invention as set forth in the following claims.

We claim:

1. A compound having the structure:

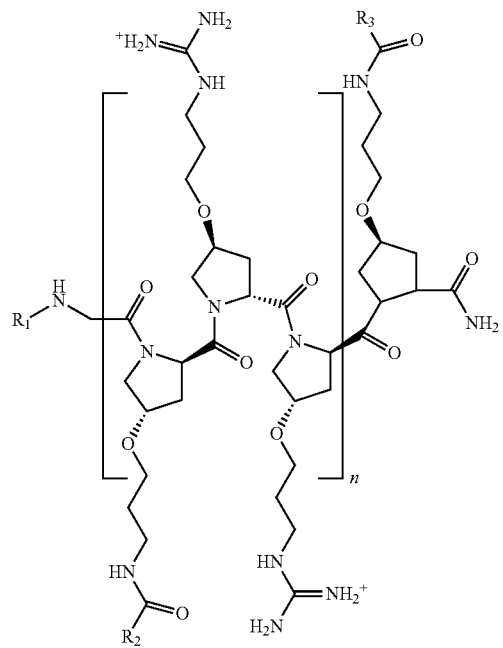

wherein R₁ is an alkyl substituent, the alkyl substituent being straight, branched or cyclic, an aryl substituent, an acyl substituent, an acetyl substituent, a dye, a fluorophore, a conjugating agent, an intracellular directing group or an antimicrobial agent;

wherein R₂ and R₃ are each independently, a hydrophobic alkyl or aryl moiety; and wherein n is from about 3 to about 10.

2. The compound of claim 1 wherein R₁ is a fluorophore.

3. The compound of claim 1 wherein R₁ is an antimicrobial agent.

4. The compound of claim 3 wherein the antimicrobial agent is kanamycin.

5. The compound of claim 1 wherein the hydrophobic alkyl moiety is linear, branched or cyclic and wherein the hydrophobic alkyl moiety comprises from at least 1 carbon atom to about 20 carbon atoms.

6. The compound of claim 1 wherein the hydrophobic aryl moiety comprises from about 5 carbon atoms to about 7 carbon atoms.

7. The compound of claim 1 wherein R₂ and R₃ are each independently n-pentyl, n-heptyl, cyclohexyl, phenyl, pmethoxyphenyl or p-nitrophenyl.

8. The compound of claim 1 wherein n is from about 3 to about 5.

9. An antimicrobial composition comprising:
at least one compound of claim 1; and
at least one buffer.

10. A compound having the structure:

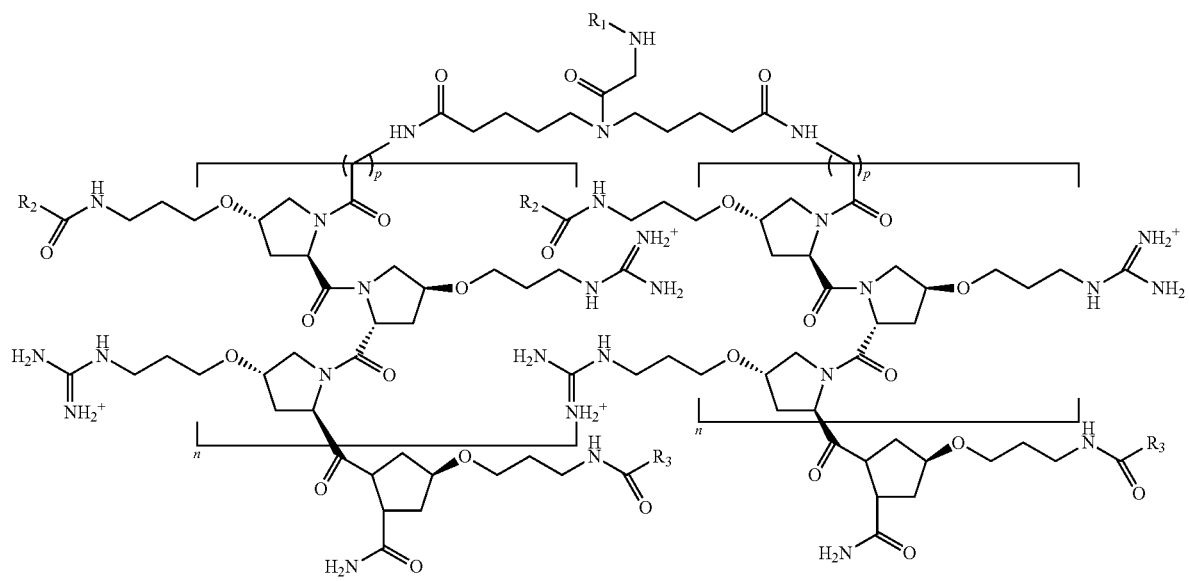

wherein R₁ is an alkyl substituent, the alkyl substituent being straight, branched or cyclic, an aryl substituent, an acyl substituent, an acetyl substituent, a dye, a fluorophore, a conjugating agent or an antimicrobial agent;

wherein R₂ and R₃ are each independently, a hydrophobic alkyl or aryl moiety;

wherein n is from about 3 to about 10; and wherein p is from about 1 to about 5.

11. The compound of claim 10 wherein R₁ is a fluorophore.

12. The compound of claim 10 wherein R₁ is an antimicrobial agent.

13. The compound of claim 3 wherein the antimicrobial agent is kanamycin.

14. The compound of claim 10 wherein the hydrophobic alkyl moiety is linear, branched or cyclic and wherein the hydrophobic alkyl moiety comprises from about 11 carbon atoms to about 20 carbon atoms.

15. The compound of claim 10 wherein the hydrophobic aryl moiety comprises from about 5 carbon atoms to about 7 carbon atoms.

16. The compound of claim 10 wherein R₂ and R₃ are each independently n-pentyl, n-heptyl, cyclohexyl, phenyl, pmethoxyphenyl or p-nitrophenyl.

17. The compound of claim 10 wherein n is from about 3 to about 5.

18. An antimicrobial composition comprising:
at least one compound of claim 10; and
at least one buffer.

* * * * *